United States Patent
Baumfalk et al.

(10) Patent No.: US 8,107,715 B2
(45) Date of Patent: Jan. 31, 2012

(54) METHOD AND DETECTION DEVICE FOR THE IMAGING DETECTION OF A SAMPLE

(75) Inventors: Reinhard Baumfalk, Goettingen (DE); Oscar-Werner Reif, Hannover (DE); Florian Wurm, Le-Mont-sur-Lausanne (CH); Maria de Jesus, Chavannes (CH); Martin Jordan, Ecublens (CH); Matthieu Stettler, Lausanne (CH); Stefan Obermann, Adelebsen (DE)

(73) Assignee: Sartorius Stedim Biotech GmbH (DE)

( * ) Notice: Subject to any disclaimer, the term of this patent is extended or adjusted under 35 U.S.C. 154(b) by 715 days.

(21) Appl. No.: 12/227,184

(22) PCT Filed: Apr. 24, 2007

(86) PCT No.: PCT/EP2007/003565
§ 371 (c)(1),
(2), (4) Date: Nov. 7, 2008

(87) PCT Pub. No.: WO2007/131595
PCT Pub. Date: Nov. 22, 2007

(65) Prior Publication Data
US 2009/0103772 A1   Apr. 23, 2009

(30) Foreign Application Priority Data
May 15, 2006 (DE) .......................... 10 2006 022 878

(51) Int. Cl.
 G06K 9/00 (2006.01)
 G06K 9/32 (2006.01)
 G06K 9/36 (2006.01)
(52) U.S. Cl. .......................... 382/141; 382/285; 382/294
(58) Field of Classification Search ........... 382/100–305
See application file for complete search history.

(56) References Cited

U.S. PATENT DOCUMENTS

| 3,914,985 | A |   | 10/1975 | von Behrens |
| 4,175,862 | A | * | 11/1979 | DiMatteo et al. ............. 356/610 |
| 5,003,488 | A |   | 3/1991 | Hardy |
| 5,013,155 | A |   | 5/1991 | Rybak |
| 5,301,238 | A | * | 4/1994 | Apter et al. .................... 382/142 |
| 5,509,090 | A | * | 4/1996 | Maruyama et al. ........... 382/276 |
| 5,644,388 | A | * | 7/1997 | Maekawa et al. ............... 356/73 |

(Continued)

FOREIGN PATENT DOCUMENTS

DE         35 20 962 A1   12/1985

(Continued)

*Primary Examiner* — Manav Seth
(74) *Attorney, Agent, or Firm* — Gerald E. Hespos; Michael J. Porco

(57) ABSTRACT

The invention relates to a device for detecting a sample in a longitudinal sample container (10), comprising a sample container holder (30) for holding the sample container in a housing. Said sample container holder comprises a side viewing window in the region of at least one longitudinal side of the sample container, and a front viewing window (35) in the region at least one front side of the sample container. Said device also comprises a first illumination arrangement for illuminating the sample container through the front viewing window, a second illumination arrangement for illuminating the sample container through the side viewing window, and an imaging photodetector for detecting a first image of the sample illuminated by means of the first illumination arrangement, and a second image of the sample illuminated by means of the second illumination arrangement. Said detection takes place through the side viewing window. Said device further comprises a digital data processing unit for overlaying the first and second images and for representing the resulting overlay image on a display device connected to the data processing unit.

13 Claims, 2 Drawing Sheets

U.S. PATENT DOCUMENTS

| | | | |
|---|---|---|---|
| 5,990,944 A * | 11/1999 | Abe | 348/215.1 |
| 6,055,329 A * | 4/2000 | Mufti | 382/152 |
| 6,222,637 B1 * | 4/2001 | Ito et al. | 358/1.18 |
| 6,479,239 B1 | 11/2002 | Anderson et al. | |
| 6,587,573 B1 * | 7/2003 | Stam et al. | 382/104 |
| 6,600,509 B1 * | 7/2003 | Kent et al. | 348/143 |
| 6,640,002 B1 * | 10/2003 | Kawada | 382/141 |
| 6,671,421 B1 * | 12/2003 | Ogata et al. | 382/284 |
| 6,762,842 B2 | 7/2004 | Pfeifer et al. | |
| 6,807,292 B1 * | 10/2004 | Goto et al. | 382/128 |
| 6,993,160 B2 * | 1/2006 | Miura et al. | 382/115 |
| 7,046,838 B1 * | 5/2006 | Sakagawa et al. | 382/154 |
| 7,313,257 B2 * | 12/2007 | Roman | 382/128 |
| 7,456,842 B2 * | 11/2008 | Kosolapov | 345/589 |
| 7,515,952 B2 * | 4/2009 | Balas et al. | 600/476 |
| 7,522,758 B2 * | 4/2009 | Ortyn et al. | 382/133 |
| 7,574,023 B2 * | 8/2009 | Sano et al. | 382/124 |
| 7,643,143 B2 * | 1/2010 | Fujii et al. | 356/336 |
| 7,756,305 B2 * | 7/2010 | Price | 382/128 |
| 2005/0163354 A1 | 7/2005 | Ziegler | |
| 2007/0140919 A1 | 6/2007 | Clarkson et al. | |

FOREIGN PATENT DOCUMENTS

| | | |
|---|---|---|
| DE | 695 18 834 T2 | 1/2001 |
| DE | 100 30 927 C1 | 5/2002 |
| DE | 102 18 693 A1 | 8/2003 |
| DE | 203 20 951 U1 | 8/2005 |
| EP | 0 754 945 B1 | 9/2000 |
| EP | 0 637 744 B1 | 11/2001 |
| EP | 1 221 607 A1 | 7/2002 |
| GB | 2 176 596 A | 12/1986 |

* cited by examiner

METHOD AND DETECTION DEVICE FOR THE IMAGING DETECTION OF A SAMPLE

The invention relates to a method for the imaging detection of a sample in a sample vessel, which is longitudinally elongate and transparent at least in sections, by means of a detection arrangement comprising:
- a sample vessel holder for stably supporting the sample vessel in a housing, with the sample vessel holder having in the region of at least one longitudinal side of the sample vessel a side viewing window which at least in sections uncovers the longitudinal side, and the sample vessel holder also having in the region of at least one end side of the sample vessel an end viewing window which at least in sections uncovers this end side,
- a first illumination arrangement comprising at least one light source for illuminating the sample and/or the sample vessel, with the light source being arranged adjacent to the end viewing window and the sample and/or the sample vessel being able to be illuminated through the end viewing window by means of the light source,
- an imaging photodetector for the imaging detection, at least in sections, of the light emitted through a side viewing window due to the illumination of the sample and/or the sample vessel,
- a digital data processing unit for image processing and controlling the photodetector.

The invention furthermore relates to a detection device for the imaging detection of a sample in a sample vessel, which is longitudinally elongate and transparent at least in sections, comprising:
- a sample vessel holder for stably supporting the sample vessel in a housing, with the sample vessel holder having in the region of at least one longitudinal side of the sample vessel a side viewing window which at least in sections uncovers the longitudinal side, and the sample vessel holder also having in the region of at least one end side of the sample vessel an end viewing window which at least in sections uncovers this end side,
- a first illumination arrangement comprising at least one light source for illuminating the sample and/or the sample vessel, with the light source being arranged adjacent to the end viewing window and the sample and/or the sample vessel being able to be illuminated through the end viewing window by means of the light source,
- an imaging photodetector for the imaging detection, at least in sections, of the light emitted through a side viewing window due to the illumination of the sample and/or the sample vessel,
- a digital data processing unit for image processing and controlling the photodetector.

U.S. Pat. No. 6,479,239 B1 discloses such methods and devices. To conduct optical measurements, generic detection devices are used in many cases, with different illumination and detection modes being used. In the process, a sample vessel, typically a cuvette or a centrifuge tube for example, is fixed in a sample vessel holder in a housing which is protected against incident surrounding light. The sample vessel holder can either be designed to directly hold a sample vessel, or comprise a separate, mobile holding unit which accommodates the sample vessel and can be inserted into a support in the housing together with the sample vessel.

Since the goal in general is to measure optical properties of a sample contained in the sample vessel, the sample vessel is usually transparent at least in the region of one or more of its side faces. The sample vessel holder, which is usually made of a non-transparent material, has one or more side viewing windows congruent to the transparent vessel faces. The side viewing windows are usually designed as mere apertures in a vessel holder wall. In this context, the terms "light", "optical" and "transparent" are not limited to the range of the electromagnetic spectrum between approximately 400 and 800 nanometers wavelength which is often referred to as the optical spectrum. In particular, when using dyes it is also possible to use light for detection which is part of the infrared or ultraviolet spectrum. The terms "optical" and "transparent" should be interpreted accordingly.

For the imaging detection of the sample, an imaging photodetector is furthermore provided which can either be arranged in the housing or attached to it in a light-proof manner. In particular, an electronic camera, such as a CCD (charge coupled device) camera, can be used as the photodetector and it is or can be connected to a digital data processing apparatus for the purposes of controlling it and for image processing and image evaluation. By way of example, the digital data processing apparatus can be an external computer, or else a microprocessor or the like integrated into the housing.

Furthermore, there is an illumination arrangement in the housing which can comprise one or more light sources. The illumination arrangement is used for defined irradiation of the sample or sample vessel with an illuminating light. The light emitted by the sample and/or the sample vessel as a result of the illumination can then be detected by the photodetector.

It is known to measure the optical reflective, transmission, fluorescent, phosphorescent and scattering properties etc. of samples/sample vessels. Accordingly, the illumination and detection beam path and their concrete components such as the illumination arrangement, side viewing window, detector etc. are intended to be adapted by a person skilled in the art.

The aforementioned U.S. Pat. No. 6,479,239 B1 discloses illuminating the sample through an end viewing window by means of a light source arranged adjacent to the end viewing window and detecting the light emitted by the sample and/or the sample vessel through a side viewing window as the basic optical configuration. As an alternative, it is suggested that the illumination and detection, which are in particular at right angles to one another, are conducted through the side viewing windows.

DE 102 18 693 A1 discloses a device in which a sample vessel is illuminated from the side and from different angles of incidence from a plurality of large-area, diffuse lamps to prevent reflections at the sample vessel wall. In the case of a vessel illuminated in this way, two photodetectors are used, on the one hand, to read a label with a sample designation and, on the other hand, to determine the level of the sample by recording an image and evaluating it.

EP 0 754 945 B1, the German translation of which is published as DE 695 18 834 T2, discloses a method for optically determining the sedimentation rate of erythrocytes in a blood sample by measuring the different positions of the phase-boundary surfaces between the plasma and the cell cake at predetermined times and by estimations based on a polynomial interpolation. The position is determined by imaging the sample vessel in the contrast image against the background illumination.

DE 35 20 962 A1 discloses a method for determining the sedimentation velocity of particles in a liquid sample which is divided amongst a plurality of sample tubes arranged in a drum which can be rotated by a motor. By illuminating the drum, the boundary surface between the liquid and the settling particles is projected reflectively onto a planar imaging photodetector, the output signal of which is read in an automated fashion and is processed for determining the sedimentation rate.

U.S. Pat. No. 5,003,488 discloses a similar method which works, however, on the basis of transmission and in which the light source is arranged in the interior of the drum to transilluminate the samples.

EP 0 637 744 B1 discloses an image processing method for recognizing patterns of agglutination in a sample.

U.S. Pat. No. 6,762,842 B2 discloses an optical configuration in which the sample vessel is illuminated through an upper end window and detection is made through an end window lying on the opposite side. However, this configuration is not suitable for imaging sample detection.

A similar optical configuration is disclosed in U.S. Pat. No. 5,013,155, which additionally describes the propagation of light in the sample vessel wall which acts as an optical waveguide using total internal reflection.

U.S. Pat. No. 3,914,985 discloses a multipart sample vessel with an outer and inner part, the inner part comprising an extended chamber and a capillary part which can be connected to the extended chamber.

DE 203 20 951 U1 discloses a single-walled sample vessel with an extended section and a capillary section connected thereto.

DE 100 30 927 C1 discloses a non-imaging bio-sensor, the sensitive element of which is designed as an optical waveguide and the total internal reflection properties of which vary as a function of the concentration of a surrounding substance to be sensed, so that measuring the optical power dissipated permits conclusions about the concentration of the substance.

The so-called PCV method is known from the field of medical diagnosis. PCV (packed cell volume) describes the proportion of solid matter in the form of a compressed cell cake compared to the total volume of a sample. Furthermore, the PCV value of the blood, referred to as the hematocrit, is known. To determine the hematocrit, a blood sample is centrifuged in a sample tube, which is usually cylindrical, until the proportion of solid matter of the blood has been deposited as a compressed cell cake on the base of the tube. The fluid part, which is also referred to as the supernate, floats on the cell cake. In order to determine the hematocrit, the volume of the cell cake is determined by measuring its height in the sample vessel, and is converted to a percentage of the overall volume of the sample.

For cell cultures with a low proportion of solid matter, sample vessels are used when determining the PCV which merge into a capillary at their bottom end, so that a scale spread is achieved in the region of the cell cake. This is intended to reduce read-out errors.

Suitable illumination is critical in particular in the case of automated measurement of the cell cake height. Known detection devices, in which illumination and detection are conducted through the side viewing windows independently of the detection mode fail easily in this case. In the region of the capillary, the ratio of wall thickness of the sample vessel to the sample thickness in the illuminating direction is very large. This means that optical signals which are solely due to the sample vessel, such as reflections, are large compared to the signal which is emitted by the sample and actually is of interest. In addition, these interference signals are amplified by the fact that the vessel wall has a high curvature in the region of the capillary because this further increases the reflections. Using sample vessels produced to a very high optical quality could provide a remedy; however, this would require a complex production using expensive materials. This is at odds with the other practical demands of the PCV tubes, which are produced as cost-effective single-use vessels made of transparent plastics.

The generic method and the generic device, in which the sample is illuminated axially, are in any case only suitable for automated sample evaluation if the sample vessels are produced very precisely and the sample support can be reproduced exactly. Using this type of illumination it is namely the case that basically only the absolute position in space of the possibly fluorescent sample can be detected, but not, however, its relation to the sample vessel, which makes the above-mentioned production precision a necessary requirement. Furthermore, the images created by the generic devices and methods which are suitable for automated evaluation are not very clear and are not suitable for visual evaluation or checking of results or for clear documentation.

It is an object of the present invention to develop the generic methods and devices in such a manner that a direct relationship between the spatial positions of the sample and the sample vessel can be created.

The first above-mentioned object is achieved in connection with the subject method for the imaging detection of a sample in a sample vessel by the fact that a second illumination arrangement with at least one light source is provided, by means of which the sample and/or the sample vessel can be illuminated through a side viewing window,
and with the method comprising the following steps:
  illuminating the sample and/or the sample vessel by means of the first illumination arrangement,
  using the photodetector to record a first image of the sample and/or sample vessel illuminated by the first illumination arrangement,
  illuminating the sample and/or the sample vessel by means of the second illumination arrangement,
  using the photodetector to record a second image of the sample and/or sample vessel illuminated by the second illumination arrangement,
  superposing the first and the second image by means of the digital data processing apparatus, and
  displaying the resultant superposed image on a display apparatus connected to the digital data processing apparatus.

Furthermore, the object is achieved in connection with the features of the preamble of claim 3 due to the fact that a second illumination arrangement with at least one light source is provided, by means of which the sample and/or the sample vessel can be illuminated through a side viewing window,
and that the photodetector is actuated such that it
  records a first image of the sample and/or sample vessel illuminated by the first illumination arrangement,
  records a second image of the sample and/or sample vessel illuminated by the second illumination arrangement, and the digital data processing unit
  superposes the first and the second image and
  displays a resultant superposed image on a display apparatus connected thereto.

The features and advantages of the device according to the invention and the method according to the invention are intended to be explained together in the following text.

The sample holder has a first end viewing window, that is to say an opening which permits illuminating light to fall onto an end face of the sample vessel. Provision is made in a corresponding manner for the illumination arrangement to be designed correspondingly. This means that it is possible for the sample or sample vessel to be illuminated through the first end viewing window of the sample vessel and that provision is made for this. This is based on the recognition that in the case of such illumination, at least a significant part of the illuminating light does not pass through the end face of the sample vessel in the normal direction, but rather is injected into the capillary walls of the sample vessel acting as an optical waveguide and propagates there according to the laws of total internal reflection. In this case there is almost perfect total internal reflection at the outer face of the capillary due to the large difference in refractive index between the material of the capillary and the surrounding medium, in general air, that is to say little or no light is output in the outward direction and captured by the detector. However, at the inner face of the capillary the step in the refractive index is much smaller because in this case there is a boundary surface to the sample, that is to say in the case of a PCV measurement to the cell cake or supernate which respectively have a significantly higher refractive index than air. It is for this reason that the limiting angle of total internal reflection with respect to the perpendicular is significantly smaller, so that light is efficiently injected into the sample and efficiently output over the entire height of the sample. This results in the sample being illuminated in its entirety perpendicularly to the capillary axis without this resulting in interfering reflections of the sample vessel wall due to conventional illumination through the side viewing windows. The overall measurement quality is significantly improved by reducing the interference.

According to the invention, provision is made for the detection device to additionally have a second illumination arrangement with at least one light source, by means of which the sample vessel can be illuminated through the side viewing window.

According to the invention, an image is recorded during illumination by the first illumination arrangement and an image is recorded during illumination by the second illumination arrangement, and these images are superposed to form a combined image. In this case, the user is shown a superposed image, which clearly depicts the sample vessel, recorded for example using conventional reflection illumination, and the measured vessel contents, that is to say the sample. An advantage of the invention, inter alia, is that the superposed image always reproduces the spatial relationship between sample and sample vessel independently of the production precision of the sample vessel or the detection device and thus permits measuring of the sample in the sample vessel independent of the absolute position in space and in a clear visual manner.

Preferably image processing algorithms are applied to the first image, that is to say the image recorded in end viewing window illumination, in the data processing apparatus for measuring and evaluating the measurement results. Such results, which can for example comprise the boundaries between cell cake and supernate or between individual cell cake sections in the case of the PCV measurement, can, in an advantageous development of the invention, be overlaid onto the displayed superposed image as graphical elements, for example as graphical boundary lines.

Preferably, provision is made for the sample vessel holder to have in the region of the lower end side of the sample vessel a first end viewing window which uncovers at least in sections the lower end side and for at least one light source of the first illumination arrangement to be arranged adjacent to the first end viewing window, by means of which the sample and/or the sample vessel can be illuminated through the first end viewing window. This is justified by the particularly efficient injection which is possible via the base area of the sample vessel, in particular when it is designed as a light injection surface.

According to a particular embodiment of the invention, provision is made for the sample vessel holder to have in the region of the upper end side of the sample vessel a second end viewing window which uncovers at least in sections the upper end side and for respectively one light source of the first illumination arrangement to be arranged adjacent to the first and the second end viewing window, by means of which the sample and/or the sample vessel can be illuminated through these end viewing windows. In other words, the core of the invention is applied to both sides in this embodiment. The sample is simultaneously illuminated from both end sides of the sample vessel. In this case, the light is injected from above via the upper edge face of the sample vessel.

Provision is preferably made for at least one light source to be an LED (light emitting diode). This is a particularly cost-effective illumination variant.

As an alternative, or additionally, provision can be made for at least one light source to be an output of an optical waveguide which can be connected to an external light generation device. This measure achieves greater flexibility of the illumination which can be matched to the specific conditions and requirements of the sample in a simple manner. LEDs can likewise be used as external light sources for reasons of cost. However, any other light source can also be used, such as lasers or discharge lamps, together with suitable filter sets, if required. Of course, it is also possible in the integrated variant to use particular filters which are required in particular for fluorescence and phosphorescence measurements.

It is preferable for the sample vessel holder to have centering shoulders which are adapted to a non-radially symmetric shape of the sample vessel. This ensures that sample vessels which are identical in construction will always be aligned in the same direction and this ensures a high reproducibility of the measurement results. Depending on the refinement of the sample vessel holder, the centering shoulders can be attached with or without separate, mobile holding devices to this support or to a support designed for direct reception of the sample vessel.

Conveniently, the sample vessel holder has a plurality of reception areas for holding one sample vessel each and each reception area is equipped with two end viewing windows and at least one side viewing window. This makes it possible to reduce the number of operational steps, in particular if, as preferably provided, the sample vessel holder can be moved by a motor in order to align the reception areas, with the motor-driven movement preferably being actuated by a programmable control unit. In the process, the samples are driven one after another into a measuring position in which they are illuminated and measured according to the invention.

Alternatively it is also possible to extend the above-mentioned illumination corresponding to the plurality of reception areas and to select the imaging optics of the photodetector in such a manner that a number of samples can be measured simultaneously. In other words, provision is made in this alternative for at least one light source of the first illumination arrangement to be assigned to each reception area to illuminate the respective sample and/or sample vessel through an assigned end viewing window.

Combinations of the specified alternatives are also conceivable.

The plurality of reception areas can preferably be arranged next to one another in a linear or annular fashion. Whereas the first variant lends itself in particular to simultaneous measurement of a plurality of samples, the second variant is suitable in particular for a motor-driven drive rotating like a drum.

Further features and advantages of the invention emerge from the following specific description and the attached drawings, which illustrate preferred embodiments of the invention in an exemplary manner, and in which FIG. 1 shows a first perspective view of an embodiment of the invention;

Figure 1:
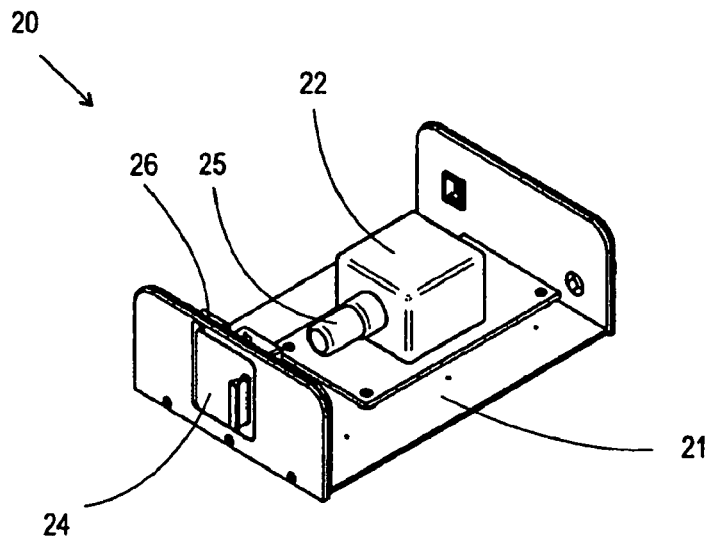
Figure 2:
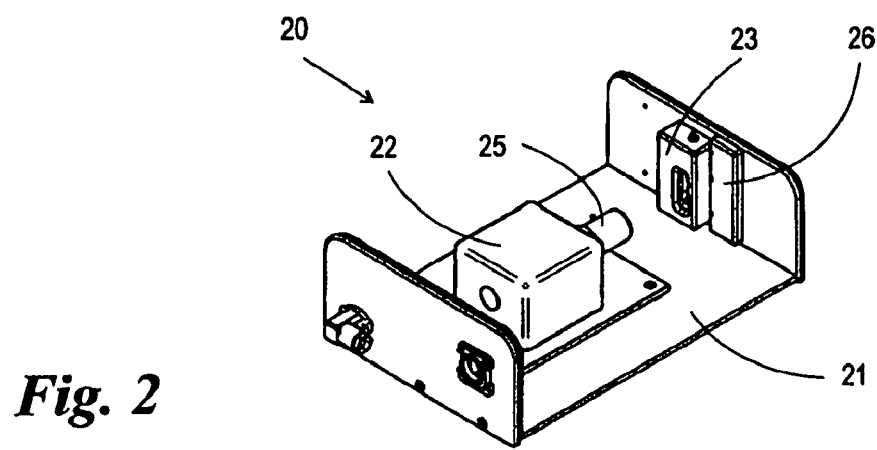
FIG. 2 shows a second perspective view of an embodiment of the invention.

FIGS. 1 and 2 show a preferred embodiment of a detection unit, subsequently referred to as a reader 20, for detecting a sample and preferably also for evaluating the detected measured values. The unit comprises a housing 21 which is preferably lightproof and of which only a lower bearing part is illustrated in FIGS. 1 and 2. A preferably provided corresponding cover is not shown in FIGS. 1 and 2. The reader 20 furthermore comprises an imaging sensor 22, which is preferably designed as a planar CCD camera. As an alternative, it is also possible that a line array or scanning photosensors is or are provided. Furthermore, the reader 20 comprises a sample support 23 which is preferably arranged on the inner side of a pivoting door 24 on one end side of the unit 20. The holding device 23 in the illustrated embodiment comprises attached to the pivoting door a support for holding a mobile holding unit 30 which is illustrated in FIG. 3 together with a sample vessel 10.

Figure 3:
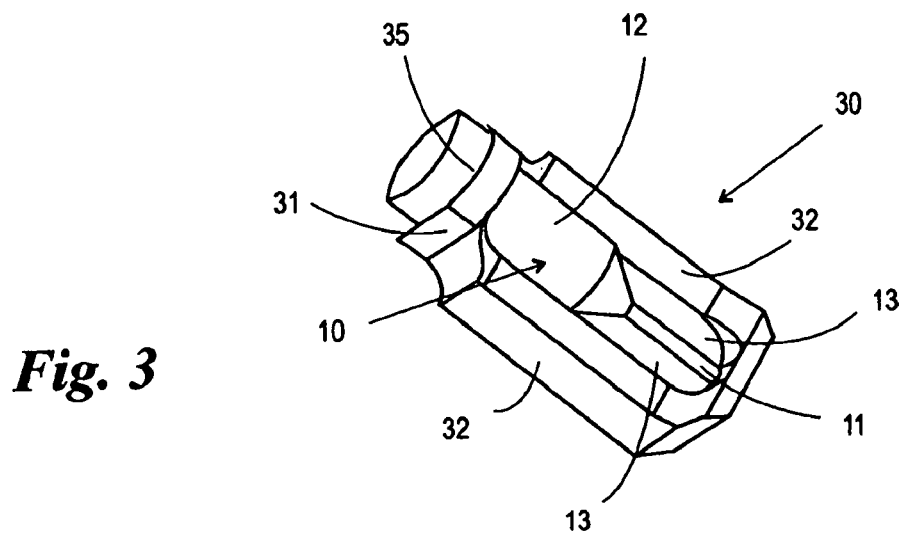
FIG. 3 shows a schematic view of a first embodiment of a mobile holding unit.

The sample vessel 10 illustrated in FIG. 3 substantially comprises a large-volume reception area 12, and connected to the bottom of this a measuring area which is designed as a capillary 11. Stabilizing wings 13 are formed on the side of the capillary 11 which break the rotational symmetry of the sample vessel 10. FIG. 3 illustrates the sample vessel 10 in a holding unit 30, which has centering shoulders matched to the stabilizing wings 13 and "covered" in FIG. 3 by the stabilizing wings 13 abutting on the former. These centering shoulders automatically bring the sample vessel 10 into a reproducible orientation when they are inserted into the holding unit 30 through the latter's opening ring 31 which also forms an upper end viewing window 35. The sample vessel 10 is aligned in the process such that an uninhibited view of the capillary 11 is ensured through a side viewing window which extends between the legs 32 of the holding unit 30.

In the preferred embodiment illustrated in FIGS. 1 and 2, the holding unit 30 and the sample vessel 10 can easily be inserted into the sample holder 23 when the door 24 is opened. Subsequent closing of the door 24 positions the sample vessel 10 opposite to the side viewing window against the sensor 22 and simultaneously closes the housing 21 in a light-proof manner.

Depending on the specific embodiment of the sensor 22 and its relative orientation to the sample holder 23, imaging optics 25 are provided which image on the sensor 22 at least the area of the sample vessel 10, in particular the area of the capillary 11. The sample vessel 10 in the sample holder 23 is illuminated by an illumination arrangement arranged below the sample holder 23 for the purposes of imaging it on the sensor 22. This is illustrated schematically in FIG. 4.

Figure 4:
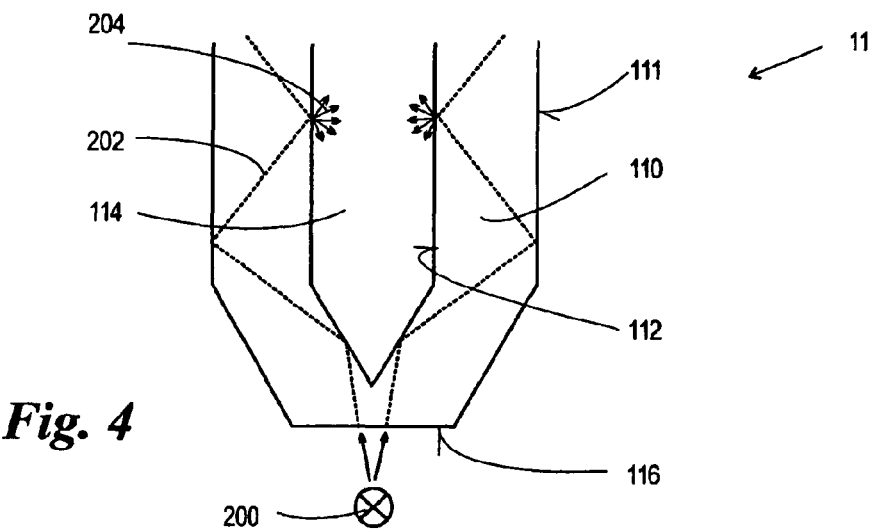
FIG. 4 shows a schematic view of a preferred method of illumination of a sample.

The lower part of the capillary 11 is illustrated in FIG. 4. The capillary wall 110 with an outer face 111 and an inner face 112 is shown schematically. The capillary wall 112 surrounds the interior region 114 which is filled by the cell cake not illustrated in FIG. 4. The interior region 114 tapers in the illustrated embodiment; this is mainly due to production processes. However, the outer side of the capillary wall 110 is flattened in the region of the tip and forms a light injection surface 116, by means of which light 202 of a light source 200 can enter the capillary wall 110. If the right choice of refractive index and injection angle is made, which the person skilled in the art can derive from known optical laws, the injected light 202 undergoes total internal reflection. The total internal reflection on the outer face 111 of the capillary wall is almost perfect due to the large difference in refractive index with respect to the surrounding air. However, on the inner face 112 of the capillary wall, which represents the boundary surface to the cell cake which is more optically dense than the surrounding air, a part of the light 202 is output into the interior region 114 of the capillary. This corresponds to illuminating the sample. The output light 204 is scattered in the sample and/or at least partly absorbed and emitted outward through the capillary wall at angles which do not generate total internal reflection (not shown in FIG. 4), where it can be detected by the photodetector 22. Hence, in the shown embodiment, the capillary wall 110 is used as an optical waveguide for the illuminating light, which illuminates the sample perpendicularly to the longitudinal extent.

Additionally, or as an alternative, corresponding illumination from above is also possible, with the annular, upper edge of the reception area 12 being able to be used as an injection surface if the edge surface is designed to be suitably flat.

Figure 5:
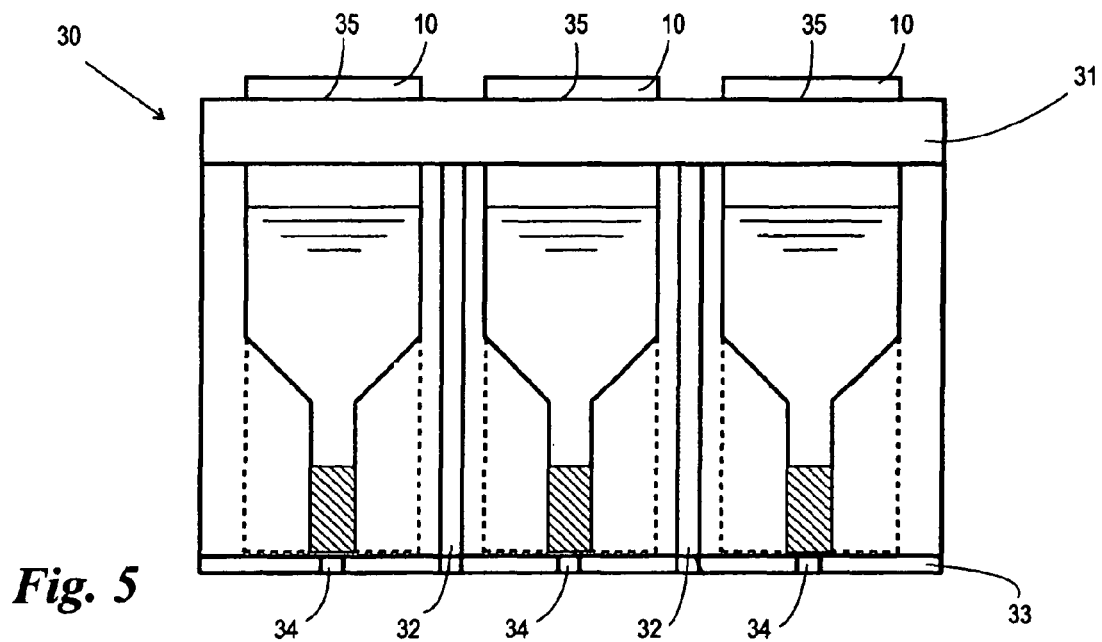
FIG. 5 shows a perspective view of a second embodiment of a mobile holding unit.

FIG. 5 shows an alternative embodiment of a holding unit 30 for holding one or more sample vessels 10. The holding unit 30 substantially comprises a covering plate 31 with recesses 35, the diameters of which substantially correspond to the outer diameter of the sample vessels 10 and which form the upper end viewing windows 35, and a base plate 33, on which the sample vessels 10 stand up on. The covering plate 31 and base plate 33 are connected by legs 32, which constitute optical insulation between the individual sample vessels 10 in a preferred embodiment of the invention. It is preferable for the front and/or backside of the holding unit 30 to remain uncovered to serve as a side viewing window and to permit observations. End viewing windows 34 in the base plate 33, which are also provided but cannot be seen in the embodiment of FIG. 3, permit illumination parallel to the direction of extent of the sample vessels 10.

The holding unit 30 can comprise an arbitrary number of chambers for holding sample vessels 10. The individual chambers are preferably dimensioned such that it is also possible to deposit conventional centrifuge tubes therein. In a particularly convenient embodiment of the holding unit 30, it is designed such that it can be inserted into commercially available centrifuges. This makes it possible to simultaneously deposit a plurality of sample vessels 10 into a centrifuge, to remove them and deposit them in the reader 20 without a further operational step.

The samples are preferably illuminated by an arrangement of one of more light emitting diodes. Alternatively, or in addition, it can be possible to have other injection possibilities for other or further light sources. By way of example, it is possible to inject external light sources, such as external lasers, via mirrors or optical fibers. Providing different injection possibilities, particularly by using standard components, makes easy and variable use of the unit 20 for different dyes and illumination requirements possible.

As an alternative to the illustrated sample holder 23, it is also possible for a number of sample holders to be provided, in particular those which are suitable for holding the previously described holders 30, with a manual or motor-driven drive conveniently being provided which permits automated sample feed and an automated sample evaluation.

The sensor 22 is preferably coupled to a digital data processing apparatus. This can be an external computer or else a microprocessor arranged in the housing 21. The data processing unit records the digital images generated by the sensor and feeds them to an evaluation process according to prescribed rules. For this purpose, suitable image processing algorithms are known to the person skilled in the art.

Of course, the embodiments discussed in the specific description and illustrated in the figures only constitute advantageous exemplary embodiments of the present invention. The person skilled in the art is provided with a broad spectrum of variation possibilities. In particular the concrete embodiment of the sample vessel holder or its holder unit 30, the selection of the sample vessels to be used and the image processing algorithms to be used, along with the particular sensor technique can be adapted to the requirements of the individual case by the person skilled in the art.

The invention claimed is:

1. A method for the imaging detection of a sample in a sample vessel (10), which is longitudinally elongate and transparent at least in sections, by means of a detection arrangement comprising:
   a sample vessel holder (23, 30) for stably supporting the sample vessel (10) in a housing (21), with the sample vessel holder (23, 30) having in the region of at least one longitudinal side of the sample vessel (10) a side viewing window which at least in sections uncovers the longitudinal side, and the sample vessel holder (23, 30) also having in the region of at least one end side of the sample vessel (10) an end viewing window (34, 35) which at least in sections uncovers this end side,
   a first illumination arrangement comprising at least one light source (200) for illuminating the sample and/or the sample vessel (10), with the light source (200) being arranged adjacent to the end viewing window (34, 35) and the sample and/or the sample vessel being able to be illuminated through the end viewing window (34) by means of the light source (200),
   an imaging photodetector (22) for the imaging detection, at least in sections, of the light emitted through a side viewing window due to the illumination of the sample and/or the sample vessel (10),
   a digital data processing unit for image processing and controlling the photodetector (22),
characterized
in that a second illumination arrangement with at least one light source is provided, by means of which the sample and/or the sample vessel (10) can be illuminated through a side viewing window, and in which the method comprises the following steps:
   illuminating the sample and/or the sample vessel (10) by means of the first illumination arrangement,
   using the photodetector (22) to record a first image of the sample and/or sample vessel (10) illuminated by the first illumination arrangement,
   illuminating the sample and/or the sample vessel (10) by means of the second illumination arrangement,
   using the photodetector (22) to record a second image of the sample and/or sample vessel (10) illuminated by the second illumination arrangement,
   superposing the first and the second image by means of the digital data processing apparatus, and
   displaying the resultant superposed image on a display apparatus connected to the digital data processing apparatus.

2. The method as claimed in claim 1, characterized in that image processing algorithms are applied to the first image in the data processing apparatus and the results of this are overlaid onto the displayed superposed image as graphical elements.

3. A detection device for the imaging detection of a sample in a sample vessel (10), which is longitudinally elongate and transparent at least in sections, comprising:
   a sample vessel holder (23, 30) for stably supporting the sample vessel (10) in a housing (21), with the sample vessel holder (23, 30) having in the region of at least one longitudinal side of the sample vessel (10) a side viewing window which at least in sections uncovers the longitudinal side, and the sample vessel holder (23, 30) also having in the region of at least one end side of the sample vessel (10) an end viewing window (34, 35) which uncovers at least in sections uncovers this end side,
   a first illumination arrangement comprising at least one light source (200) for illuminating the sample and/or the sample vessel (10), with the light source (200) being arranged adjacent to the end viewing window (34, 35) and the sample and/or the sample vessel being able to be illuminated through the end viewing window (34) by means of the light source (200),
   an imaging photodetector (22) for the imaging detection, at least in sections, of the light emitted through a side viewing window due to the illumination of the sample and/or the sample vessel (10),
   a digital data processing unit for image processing and controlling the photodetector (22),
characterized
in that a second illumination arrangement with at least one light source is provided, by means of which the sample and/or the sample vessel (10) can be illuminated through a side viewing window, and in that the photodetector (22) is actuated such that it
   records a first image of the sample and/or sample vessel (10) illuminated by the first illumination arrangement,
   records a second image of the sample and/or sample vessel (10) illuminated by the second illumination arrangement, and the digital data processing unit
   superposes the first and the second image and
   displays a resultant superposed image on a display apparatus connected thereto.

4. The detection device as claimed in claim 3, characterized in that the sample vessel holder (30) has in the region of the lower end side of the sample vessel (10) a first end viewing window (34) which uncovers at least in sections the lower end side and at least one light source (200) of the first illumination arrangement is arranged adjacent to the first end viewing window (34), by means of which the sample and/or the sample vessel can be illuminated through the first end viewing window (34).

5. The detection device as claimed in claim 4, characterized in that the sample vessel holder (30) has in the region of the upper end side of the sample vessel (10) a second end viewing window (35) which uncovers at least in sections the upper end side and a light source of the first illumination arrangement is arranged adjacent to the second end viewing window (35), by means of which the sample and/or the sample vessel can be illuminated through the second end viewing window (34).

6. The detection device as claimed in claim 3, characterized in that at least one light source (200) is an LED.

7. The detection device as claimed in claim 3, characterized in that at least one light source is an output of an optical waveguide which can be connected to an external light generation device.

8. The detection device as claimed in claim 3, characterized in that the sample vessel holder (23, 30) has centering shoulders which are adapted to a non-radially symmetric shape of the sample vessel.

9. The detection device as claimed in claim 3, characterized in that the sample vessel holder (30) has a plurality of reception areas for holding one sample vessel (10) each and each reception area is equipped with a first end viewing window (34) and at least one side viewing window.

10. The detection device as claimed in claim 9, characterized in that at least one light source of the first illumination arrangement is assigned to each reception area to illuminate the respective sample and/or sample vessel through an assigned end viewing window (34, 35).

11. The detection device as claimed in claim 9, characterized in that the sample vessel holder (30) can be moved by a motor in order to align the reception areas.

12. The detection device as claimed in claim 9, characterized in that the reception areas are arranged linearly next to one another.

13. The detection device as claimed in claim 9, characterized in that the reception areas are arranged annularly.

* * * * *